United States Patent [19]

Bayers

[11] 4,316,293
[45] Feb. 23, 1982

[54] FLEXIBLE INTRAOCULAR LENS

[76] Inventor: Jon H. Bayers, 2935 Bechelli La., Suite C, Redding, Calif. 96001

[21] Appl. No.: 241,205

[22] Filed: Mar. 6, 1981

Related U.S. Application Data

[63] Continuation-in-part of Ser. No. 70,034, Aug. 27, 1979, Pat. No. 4,257,130.

[51] Int. Cl.³ ............................ A61F 1/16; A61F 1/24
[52] U.S. Cl. ............................................................ 3/13
[58] Field of Search .......................................... 3/13, 1

[56] References Cited

U.S. PATENT DOCUMENTS

| | | | |
|---|---|---|---|
| 3,925,825 | 12/1975 | Richards et al. | 3/13 |
| 4,056,855 | 11/1977 | Kelman | 3/13 |
| 4,073,015 | 2/1978 | Peyman et al. | 3/13 |
| 4,092,743 | 6/1978 | Kelman | 3/13 |
| 4,159,546 | 7/1979 | Shearing | 3/13 |
| 4,174,543 | 11/1979 | Kelman | 3/13 |
| 4,254,511 | 3/1981 | Chase et al. | 3/13 |

FOREIGN PATENT DOCUMENTS 1103399  5/1955  France .................................. 3/13

OTHER PUBLICATIONS

"Experience With Twelve Cases Of Intra-ocular Anterior Chamber Implants For Aphakia" by J. Boberg-ANS, British Journal Of Ophthalmology, vol. 45, No. 1, Jan. 1961, pp. 37–43.

Primary Examiner—Ronald L. Frinks
Attorney, Agent, or Firm—Bielen and Peterson

[57] ABSTRACT

An intraocular lens for placement in either the anterior or posterior chamber of the eye which employs a lens portion intended for placement adjacent a side of the iris and at least one flexible appendage extending from the lens portion to the extreme periphery of the iris.

13 Claims, 6 Drawing Figures

FLEXIBLE INTRAOCULAR LENS

BACKGROUND OF THE INVENTION

The present application is a continuation-in-part application of application Ser. No. 70,034, filed Aug. 27, 1979, now U.S. Pat. No. 4,257,130.

The present invention relates to a novel intraoocular lens mechanism for placement within the eye which is particularly useful for insertion of the same within the posterior chamber of the eye.

Intraocular lens implantation has evolved into the preferred method of remedying the correction of vision, particularly after cataract removal. In this regard, reference is made to U.S. Pat. Nos. 4,134,160 and 4,134,161 to Bayers which describe intraocular lenses having an adjustability factor which aids in the proper fitting of the lenses. A recent development embodied in U.S. Pat. No. 4,159,546 issued to Shearing, describes an intraocular lens having a pair of springy legs which fit into the ciliary sulcus in the posterior chamber of the eye. The Shearing lens, based on the original Choyce lens, requires extra capsular cataract surgery before insertion. It may be seen that the Shearing lens is quite difficult to insert directly into the ciliary sulcus since the surgeon is not able to see the springy arms during insertion. Moreover, earlier lenses such as the lens described in U.S. Pat. No. 3,906,551 issued to Otter, are susceptible to dislocation during inflammation of an eye. Such a condition causes a synache or undersirable adhesion of a portion of the lens generally to the iris surrounding the pupil. Dilation of the eye is often chemically induced by the surgeon for the purposes of postoperative treatment of the eye. Although posterior chamber fixation of an intraocular lens has many disadvantages, it has been favored since endothelial touch is greatly reduced or eliminated.

An intraocular lens is needed which will obtain visible fixation yet be optically positioned in the posterior chamber without endangering the endothelium and without being susceptible to synache dislocation.

Anterior chamber angle fixation lenses alleviate insertion difficulties and can be used with intra capsular surgery. The angle supported anterior chamber lenses do not depend upon the iris for support and can not dislocate posteriorally into the vitreous cavity. Prior rigid anterior chamber lenses have been accompanied by higher incidences of uveitis, iritis and glaucoma and are sometimes accompanied by a presisting eye tenderness for months to years. The exact dimension of rigid anterior chamber lenses is critical since lenses of too short a diameter dislocate or "propellar" in the anterior chamber. These lenses need to be sized precisely, generally requiring the presence of 3 sterile lenses at the time of surgery.

A flexible anterior chamber lens is needed which will obtain visible fixation and fit all normally sized eyes. The lens should be easily insertable and have looped configurations preventing anterior displacement, causing damage to the corneal endothelium. Full dilation should be possible without dependence upon the iris for fixation.

SUMMARY OF THE INVENTION

In accordance with the present invention a novel intraocular lens mechanism is provided which solves the problems heretofore described.

The lens of the present application employs a lens portion of optical zone which may be placed in the posterior chamber of the eye immediately following cataract removal. The lens portion is designed to be placed adjacent the iris and includes a pair of appendages, each one of which is fastened to the lens portion. Each appendage includes a first portion which passes through the pupil of the eye and a second portion connected to the first portion which extends along the other side of the iris for contact with the peripheral area of the anterior chamber, namely the angle found between the cornea and iris. Each of the appendages may be formed into a closed loop where the first portion takes the form of a pair of posts which extend through the pupil from the lens portion. The remainder of the loop is fastened to the ends of the posts and extends angularly therefrom to the angle of the eye. The loops may be formed such that one of the same may include an end portion having two areas intended for contact with the periphery of the eye. In this manner, the lens of the present application would obtain three point or four point fixation.

To prevent endothelial touch the loops may be formed as elongated members having an oval cross-sectional configuration. In this manner, any force directed at the end portions of the loops would cause the appendage to spread laterally, generally normal to the optical axis of the lens and pupil rather than vertically inwardly or outwardly in relation to the plane of the iris.

In another embodiment the lens of the present invention may include a lens portion having at least one appendage fastened thereto. The appendage has a loop terminating in an outer end and a first portion fastened to the lens portion. A second portion of the appendage connects to the first portion of the appendage and extends therefrom along a side of the iris. The outer end of the second portion of the appendage contacts the extreme periphery of the eye. Again, means for restricting flexure would be included which may externalize in a flattened or oval cross-sectional configuration of the appendage. Such a lens may be placed in the anterior chamber immediately following cataract surgery or at a later surgery. The embodiment could be also placed in the posterior chamber if an extra capsular surgery were performed. The flexibility of the at least one loop would allow for variation in ocular size. A loop or loops could be formed such that one of the same may include an end portion having two areas intended for contact with the periphery of the eye. In this matter, the lens of the present application would obtain 3 point or 4 point fixation.

In the foregoing summary it may be seen that a novel and useful intraocular lens mechanism has been described.

It is therefore an object of the present invention to provide an intraocular lens mechanism which may have a lens portion positioned in the posterior chamber of the eye without the necessity of extra capsular cataract surgery.

It is another object of the present invention to provide an intraocular lens mechanism which derives fixation from the anterior chamber of the eye which permits the observation of the actual fixation by the surgeon.

It is yet another object of the present invention to provide an intraocular lens mechanism which permits the dilation of the iris postoperatively without endangering the fixation of the intraocular lens.

Another object of the present invention is to provide an intraocular lens mechanism which includes means for preventing endothelial touch by the physical structure of the intraocular lens at any time after implantation.

It is yet another object of the present invention to provide an intraocular lens mechanism which may be positioned in the anterior chamber or in the posterior chamber of an eye of an extra capsular extraction.

It is another object of the invention to provide an intraocular lens mechanism which provides fixations in the anterior chamber of the eye which permits the observation of the actual fixation by the surgeon.

It is another object of the present invention to provide a lens which provides for proper fixation with all normally sized eyes.

It is another object of the present invention to provide an intraocular lens mechanism which includes means for prevention of endothelial touch through the physical structure and configuration of the loops of the lens.

The invention possesses other objects and advantages especially as concerns particular characteristics and features thereof, which will become apparent as the specification continues.

For a better understanding of the invention, reference is made to the following detailed description.

DESCRIPTION OF THE PREFERRED EMBODIMENTS

Various aspects of the present invention will evolve from the following detailed description of the preferred embodiments thereof, which should be taken in conjunction with the heretofore described drawings.

Figure 1:
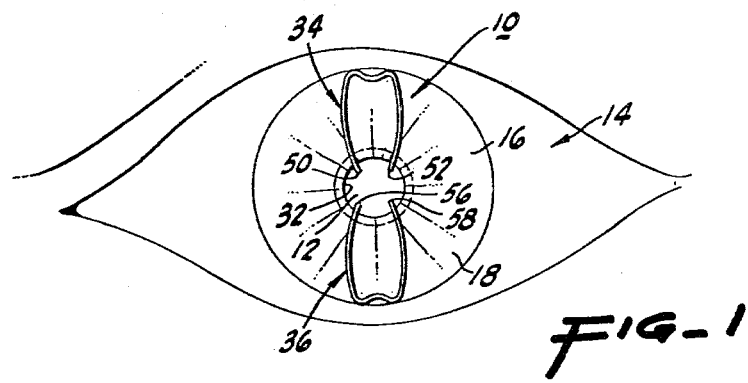
FIG. 1 is a top plan view of the lens mechanism on the present invention implanted in a human eye.
Figure 2:
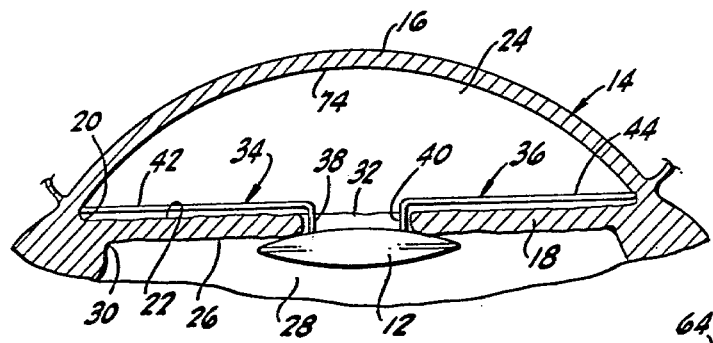
FIG. 2 is a sectional view showing the lens mechanism of the present invention implanted in a human eye.

With reference to the drawings, FIG. 1 shows the lens mechanism of the present invention and is identified herein by reference character 10. Lens mechanism 10 includes a lens portion or optical zone 12 having an optical axis generally coaxial with the pupillary axis which may be constructed of any suitable material which is nonreactive to human tissue. For example, ophthalmic glass, and plastic such as polymerized methylmethacrylate and the like are adequate. Lens portion 12 may take the form of a convex, plano-convex, or other lens shape necessary to correct the vision of eye 14 immediately following cataract removal. FIG. 2 most clearly shows eye 14 having a cornea 16 and an iris 18 which form an angle 20 therebetween. Iris 18 has a first side 22 lying in anterior chamber 24 and a second side 26 lying in posterior chamber 28. Lens mechanism 10 is shown in FIG. 2 in place within eye 14 following intracapsular cataract surgery. It should be noted that lens mechanism 10 may be employed to correct aphakia following extra capsular cataract surgery as well. Eye 14 also includes ciliary sulcus 30 where the lenses of the prior art are now fixed. As can be seen, ciliary sulcus is not visible from the surgeon's point of view outside of cronea 16. FIG. 2 also illustrates the position of pupil 32 formed by iris 18.

Lens mechanism 10 also includes a first appendage 34 and a second appendage 36 extending from lens portion 12. Although appendages 34 and 36 are depicted as identical in the drawings, certain variations as to shape may cause one appendage to be formed differently from the other appendage. Each appendage 34, 36 includes a first portion 38 and 40 which is fastened to lens portion 12 by gluing, heat or sonic welding, moulding, or any other method known in the art. First potions 38 and 40 pass through pupil 32 of eye 14 and connect to second portions 42 and 44 of appendages 34 and 36 respectively. Second portions 42 and 44 extend along side 22 of iris 18 and contact angle 20 of eye 14 at the periphery of eye 14. In contrast, lens portion 12 remains in posterior chamber 28 against side 26 of iris 18. Turning to FIG. 1, it may be seen that appendages 34 and 36 may take the form of elongated members 46 and 48 formed in a closed loop. In such a case first portion 38 would include a pair of posts 50 and 52, FIG. 1, fastened to lens portion 12, extending through pupil 32, and fastened to continuous member 54 to complete the loop. It should be noted that elongated member 48 also includes a pair of posts 56 and 58 as well as a continuous member 60. It is fully contemplated that first and second appendages 34 and 36 may be open rather than looped.

Figure 3:
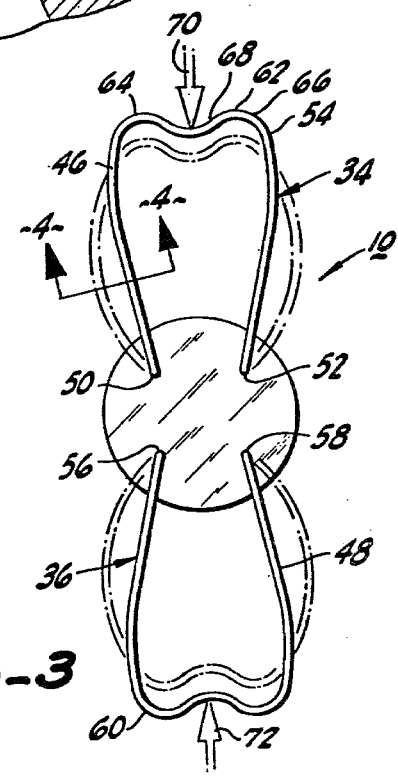
FIG. 3 is a top plan view of the lens mechanism of the present invention showing deformation of its appendages upon the application of force.

Turning to FIG. 3, it may be seen that at least one loop member 46 may include an end portion 62 having areas 64 and 66 which bulge outwardly in relation to indent portion 68. Thus, areas 64 and 66 of end portion 62 would make contact with angle 20 while indent portion 68 generally would not. Appendage 36 may be formed without the bulged areas 64 and 66 of appendage 34 to create a three point fixation. Likewise, as shown in FIG. 3, apendage 36 may be formed identically to appendage 34 creating a four point fixation at angle 20. Arrows 70 and 72 represent an effective force on appendages 34 and 36; the actual force would normally be on the bulged areas of appendages 34 and 36, e.g. areas 64 and 66 of appendage 34.

Figure 4:
FIG. 4 is a view taken along line 4—4 of FIG. 3.

Turning to FIG. 4, it may be seen that elongated members 46 and 48 have an oval cross-sectional configuration. As a result of this feature, force 70 and 72 cause appendages 34 and 36 to expand laterally across the top of side 22 of iris 18 in a direction generally normal to the optical axis of the lens and pupil rather than upwardly toward cornea 16 and endothelium layer 74. It may be apparent that endothelium layer 74 will not be touched by appendages 34 and 36 and therefore will not be damaged by the same post-operatively. FIG. 3 depicts the lateral movement of appendages 34 and 36 in phantom.

Figure 5:
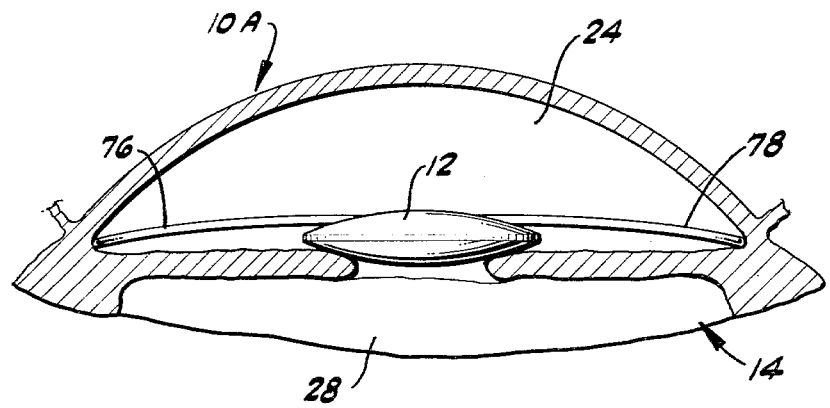
FIG. 5 is a sectional view of an embodiment of the present invention placed in the anterior chamber of the eye.
Figure 6:
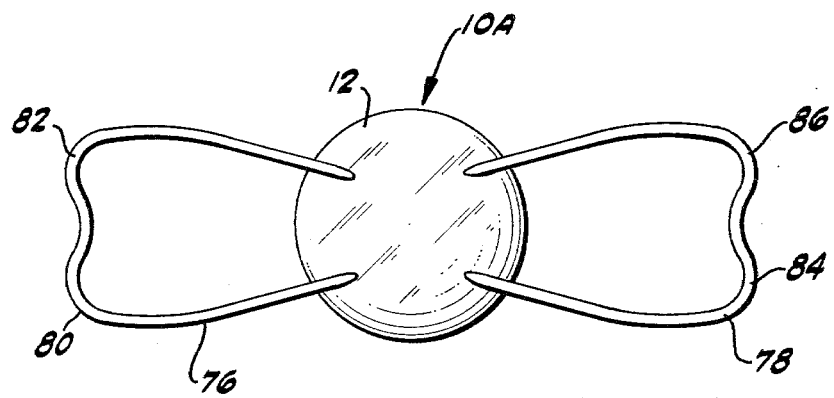
FIG. 6 is a top plan view of an embodiment of the present invention.

FIG. 5 shows another lens embodiment 10A of the present invention where lens portion 12 includes appendages 76 and 78 which extend to the angle 20. It should be noted that lens portion 12 and appendages 76 and 78 are located in the anterior chamber 24 of eye 14. It is intended that lens 10A may be similarly placed in the posterior chamber 28 between portions of the ciliary sulcus 30. Appendages 76 and 78 may be flattened as shown in FIG. 4 to resrict flexture of the same laterally in relation to iris 18 as shown in FIG. 3. Bulge areas 80, 82, 84, and 86, likewise, add purchase to the lens 10A, FIG. 6.

In operation, the surgeon opens cornea 16 in the usual manner and inserts lens mechanism 10 within eye 14. Appendage 34 and appendage 36 are placed within the confines of angle 20 and lens portion 12 is forced through pupil 32 which may be dilated to greatly facilitate this maneuver. Lens 10A is simply placed either in anterior chamber 24 or posterior chamber 28 if the posterior capsule is present, between opposing sides of angle 20 of ciliary sulcus 30 respectively. After insertion, lens mechanism 10 or 10A will not effect any dilation of pupil 32 and the fixation of appendages 34 and 36 will always be visible to surgeon.

While in the foregoing specification embodiments of the invention have been set forth in considerable details for the purposes of making a complete disclosure of the invention, it will be apparent to those of ordinary skill in the art that numerous changes may be made in such details without departing from the spirit and principles of the invention.

What is claimed is:

1. An intraocular lens for placement within an eye comprising:
   a. a lens portion having an optical axis for placement adjacent one side of the iris;
   b. at least one appendage, said at least one appendage being fastened to said lens portion and including a loop, terminating with an outer end, having a first portion fastened to said lens portion, and a second portion connected to said first portion and intended for extending therefrom along a side of the iris into contact with the extreme periphery of the eye with said outer end;
   c. means for restricting flexure of said loop vertically inwardly or outwardly in relation to the plane of the iris while allowing lateral flexure generally normal to said optical axis in response to forces directed to said outer end along said eye periphery.

2. The intraocular lens of claim 1 in which said loop comprises a closed loop.

3. The intraocular lens of claim 2 in which said loop includes an end portion to be located at the periphery of the eye having two areas at said outer end intended for contact with the periphery of the eye.

4. The intraocular lens of claim 1 in which said means for restricting flexure of said loop comprises said second portion having a cross-sectional configuration with at least a long dimension and a relatively shorter dimension, said relatively shorter dimension being oriented substantially normal to said optical axis for placement along a side of the iris.

5. The intraocular lens of claim 4 in which said second portion of said loop possesses an oval cross-sectional configuration.

6. The intraocular lens of claim 1 in which said at least one appendage comprises a first appendage and said intraocular lens further comprises a second appendage fastened to said lens portion.

7. The intraocular lens of claim 6 in which said second appendage includes a loop, terminating with an outer end, having a first portion fastened to said lens portion, and a second portion connected to said first portion and intended for extending therefrom along a side of the iris into contact with the extreme periphery of the eye with said outer end.

8. The intraocular lens of claim 7 in which said means for restricting flexure of said loop comprises means for restricting flexure of said loop of said first appendage and further comprises said second portion of said loop of said first appendage having a cross-sectional configuration with at least a long dimension and a relatively shorter dimension, said relatively shorter dimension being oriented substantially normal to said optical axis for placement along a side of the iris.

9. The intraocular lens of claim 8 in which at least one of said loops includes an end portion to be located at the periphery of the eye having two areas at said outer end intended for contact with the periphery of the eye.

10. The intraocular lens of claim 9 in which said second portion of said loop of said first appendage possesses an oval cross-sectional configuration.

11. The intraocular lens of claim 10 in which said loop comprises a closed loop of said first appendage.

12. The intraocular lens of claim 11 which additionally comprises means for restricting flexure of said loop of said second appendage vertically inwardly or outwardly in relation to the plane of the iris while allowing lateral flexure generally normal to said optical axis in response to forces directed to said outer end along said eye periphery.

13. the intraocular lens of claim 12 in which said loop of said second appendage comprises a closed loop.

* * * * *